(12) United States Patent
Payne, Jr. et al.

(10) Patent No.: US 6,264,548 B1
(45) Date of Patent: Jul. 24, 2001

(54) DISPENSING SYSTEM AND METHOD

(75) Inventors: Robert V. Payne, Jr., Pittsburgh; Irvin L. Parr, Jr., Verona, both of PA (US)

(73) Assignee: Transcents, Inc., Pittsburgh, PA (US)

( * ) Notice: Subject to any disclaimer, the term of this patent is extended or adjusted under 35 U.S.C. 154(b) by 0 days.

(21) Appl. No.: 09/396,394

(22) Filed: Sep. 15, 1999

(51) Int. Cl.[7] .................................................. B60H 3/00
(52) U.S. Cl. .......................... 454/157; 422/123; 422/124
(58) Field of Search ................................. 454/157, 337, 454/75; 422/123, 124

(56) References Cited

U.S. PATENT DOCUMENTS

| D. 361,375 | 8/1995 | Gallagher et al. ............... D23/366 |
|---|---|---|
| 3,139,218 | 6/1964 | Cairelli .................................... 222/70 |
| 3,259,050 | * 7/1966 | Grimm, III ........................ 454/157 |
| 3,351,240 | 11/1967 | Gray ....................................... 222/70 |
| 3,891,149 | 6/1975 | Rendemonti ......................... 239/70 |
| 3,974,941 | 8/1976 | Mettler .................................. 222/70 |
| 4,433,796 | 2/1984 | Brooks, Jr. ......................... 222/135 |
| 4,601,886 | 7/1986 | Hudgins .............................. 422/116 |
| 4,867,045 | * 9/1989 | Freedman ............................ 454/157 |
| 5,078,046 | * 1/1992 | Mascolo et al. ..................... 454/157 |
| 5,221,025 | 6/1993 | Privas ....................................... 222/1 |
| 5,223,182 | * 6/1993 | Steiner et al. .................... 422/124 X |
| 5,433,660 | * 7/1995 | Ohba ...................................... 454/75 |
| 5,882,256 | * 3/1999 | Shropshire ........................... 454/157 |
| 6,137,404 | * 10/2000 | O'Connor ....................... 454/128 X |

FOREIGN PATENT DOCUMENTS 63-279922 * 11/1988 (JP) ..................................... 454/157

* cited by examiner

Primary Examiner—Harold Joyce
(74) Attorney, Agent, or Firm—Andrew J. Cornelius (57) ABSTRACT

A dispensing system for dispensing a deodorizing, disinfecting or freshening substance is mounted in the heating and air conditioning ductwork of a vehicle, and includes an electronic controller that controls the operation of the system. The substance dispensed by the system is spread through the ductwork throughout the interior of the vehicle by the heating and air conditioning system of the vehicle. The system is operated during a cycle that includes an ON time, during which the substance is dispensed, and an OFF time, during which the substance is not dispensed. The system is configured to cycle only when the vehicle ignition is on. The system can also be configured to cycle only when the parking brake is released, or when the vehicle transmission is in gear.

15 Claims, 8 Drawing Sheets

DISPENSING SYSTEM AND METHOD

BACKGROUND OF THE INVENTION

The present invention relates to dispensing, and, more particularly, to a system and method for dispensing, and preferably for spraying, a liquid into a confined space.

Today, most confined inhabited spaces, including buildings, rooms and vehicle interiors, are heated and air conditioned. Typically, there is relatively little exchange of air between these spaces and the outdoors. As a result, odors from the people in the spaces, their clothing and food, and other sources tend to accumulate in these spaces, making the air in the spaces unpleasant to breathe.

Deodorizers, air fresheners and disinfectants have, of course, been used for some time. They are typically dispensed manually from aerosol or pump dispensers by depressing a button that releases a liquid substance from the dispenser into the space, or continuously by an evaporative type dispenser from which a substance evaporates into the air. The effects of aerosol and pump dispensers are relatively short-lived, being limited to a relatively short duration following the release of the dispensing button. Accordingly, long term effects can be achieved with an aerosol or pump dispenser only by continually and manually operating the dispenser, which is burdensome and provides inconsistent results over time. The effects of evaporative type dispensers are longer lasting, but their effects lessen with time and, accordingly, do not provide a consistent result over time. Neither approach is effective for providing a space with a relatively consistent level of deodorizing, freshening or disinfecting over a long period of time. Finally, relatively large spaces, like building interiors and the passenger compartments of buses and aircraft, cannot be deodorized, freshened or disinfected using manual or evaporative dispensers due to the limited space that can be affected by these dispensers. There is, therefore, a need for a dispensing system that can provide a consistent effect in large spaces over a long period of time. There is also a need for a dispensing system the operation of which can be affected by parameters existing in the space to conserve the substance being dispensed.

SUMMARY OF THE INVENTION

The present invention provides a system and method for dispensing such substances as deodorizers, air fresheners and disinfectants. The present invention can be used to dispense substances consistently throughout a large space over a long period of time.

The present invention provides a dispenser including a canister including a body that contains a substance to be dispensed from the canister, a nozzle through which the substance is dispensed and an actuator mounted to the nozzle. Preferably, the canister is an aerosol canister, and the nozzle includes an actuator button to which the actuator is mounted. The actuator can be an electrical actuator.

The present invention also provides a dispensing system for dispensing a substance including a canister including a body that contains a substance to be dispensed from the canister, a nozzle through which the substance is dispensed, an electric actuator mounted to the nozzle, and a controller that controls dispensing of the substance from the canister. Preferably, the controller is an electrical controller that controls operation of the canister during a dispensing cycle that includes an ON time during which the controller actuates the actuator to dispense the substance from the canister, and an OFF time during which the controller deactivates the actuator to stop dispensing of the substance from the canister. Preferably, the system is mounted in the heating and air conditioning ductwork of the vehicle to permit the heating and air conditioning system of the vehicle to convey the substance throughout the interior of the vehicle. Preferably, the dispensing cycle occurs only if the ignition system of the vehicle is on. Alternately, the dispensing cycle can occur only when the parking brake of the vehicle is released, or when the vehicle is in gear.

The present invention also provides a method for dispensing a substance including the steps of mounting a dispenser containing the substance in the space in which the substance is to be dispensed, mounting an actuator in operable relationship with the dispenser, actuation of the actuator causing the dispenser to dispense the substance, and actuating the dispenser cyclically, each cycle including an on time of a preselected duration during which the actuator is actuated to cause dispensing, and an off time of a preselected duration during which the actuator is not actuated. Preferably, the dispenser is mounted in the ductwork of a vehicle to permit the heating and air conditioning systems of the vehicle to disperse the dispensed substance throughout the interior of the vehicle, and the dispenser is actuated only when the vehicle ignition is on. Alternately, the dispenser can be actuated only when the vehicle parking brake is released, or when the vehicle is in gear.

BRIEF DESCRIPTION OF THE DRAWING

The following detailed description of the preferred embodiments may be understood better if reference is made to the appended drawing, in which.

DETAILED DESCRIPTION OF THE PREFERRED EMBODIMENT

Figure 1:
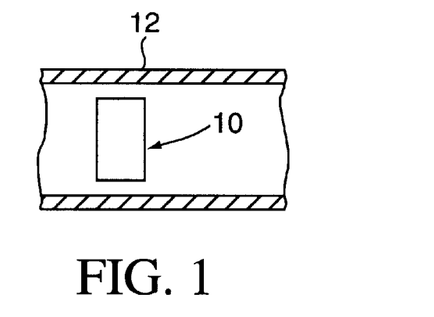
FIG. 1 is a diagrammatic view of a dispensing system provided by the present invention installed in the heating and air conditioning ductwork of a bus.

FIG. 1 shows a dispenser system 10 provided by the present invention installed in the ductwork 12 of a bus. Generally, system 10 cyclically sprays a deodorizing, air freshening or disinfecting substance from an aerosol container 20 into the ductwork 12 of the bus or other vehicle, and the heating or air conditioning system of the vehicle distributes the substance throughout the interior of the bus with the heated or cooled air. An electrically operated actuator 14 actuates the nozzle 18 of the aerosol container 20 to spray the substance in the ductwork 12. System 10 operates cyclically on a cycle defined by an ON spray time or period, during which system 10 causes container 20 to spray substance into ductwork 12, and an OFF spray time or period, during which system 10 does not cause container 20 to spray substance. The range provided for the ON time period is 1 to 5 seconds, and the range provided for the OFF time period is 1 to 30 minutes. The ON time of the cycle begins when system 10 causes electrically operated actuator 14 to actuate nozzle 18 to begin spraying the substance through nozzle 18 into ductwork 12. The ON time ends upon expiration of a period of preselected length, which can be adjusted by the user. The OFF time of the cycle begins at the expiration of the ON time, and ends upon expiration of another period of preselected length, which also can be adjusted by the user. System 10 counts the number of ON times or cycles for container 20. When the count reaches the maximum ON time count, system 10 assumes that container 20 is empty, and disables further dispensing until the container 20 is removed and replaced, and illuminates an indicator light that alerts the user to replace container 20 with a full container 20. The maximum ON time count, which is the number of ON time cycles that system 10 permits before requiring replacement of a container 20, is set by the user. The range for the maximum ON time count is 1,500 to 2,500 ON times or cycles, and is set by the user at the expected number of sprays of a duration equal to the ON time that can be expected from a particular container 20 before the substance is depleted. A reset switch 44 is depressed by the insertion of the full container 20, which enables system 10 to continue dispensing. A warning light is illuminated when the ON time count approaches the maximum ON time count permitted by system 10. This warning ON time count is also set at the factory. System 10 includes a controller 22 that is mounted on a PC board 77, which in turn is mounted on a mounting 79 that is mounted within the system housing 24. Controller operates from a 24 volt DC supply derived directly from the bus ignition when the ignition is on. The controller includes a system reset switch 26, which is accessible only to the user, that is used to reset the ON time count when a container 20 must be replaced prior to its ON time count reaching the maximum ON time count.

System 10 can be configured to make it responsive to various conditions in the bus. In its simplest form, operating power is made available to system 10 when the bus ignition is on, which renders system 10 operational to cyclically dispense the substance. Alternatively, power can be made available to system 10 only when the bus ignition is on and either the bus transmission is in gear or the parking brake of the bus is released. Accordingly, system 10 can be configured to cyclically spray the substance into ductwork 12 only when the ignition is on, only when the ignition is on and the parking brake is off, only when the ignition is on and the bus is in gear, or at any other time that is controlled by other conditions occurring on the bus.

Figure 2:
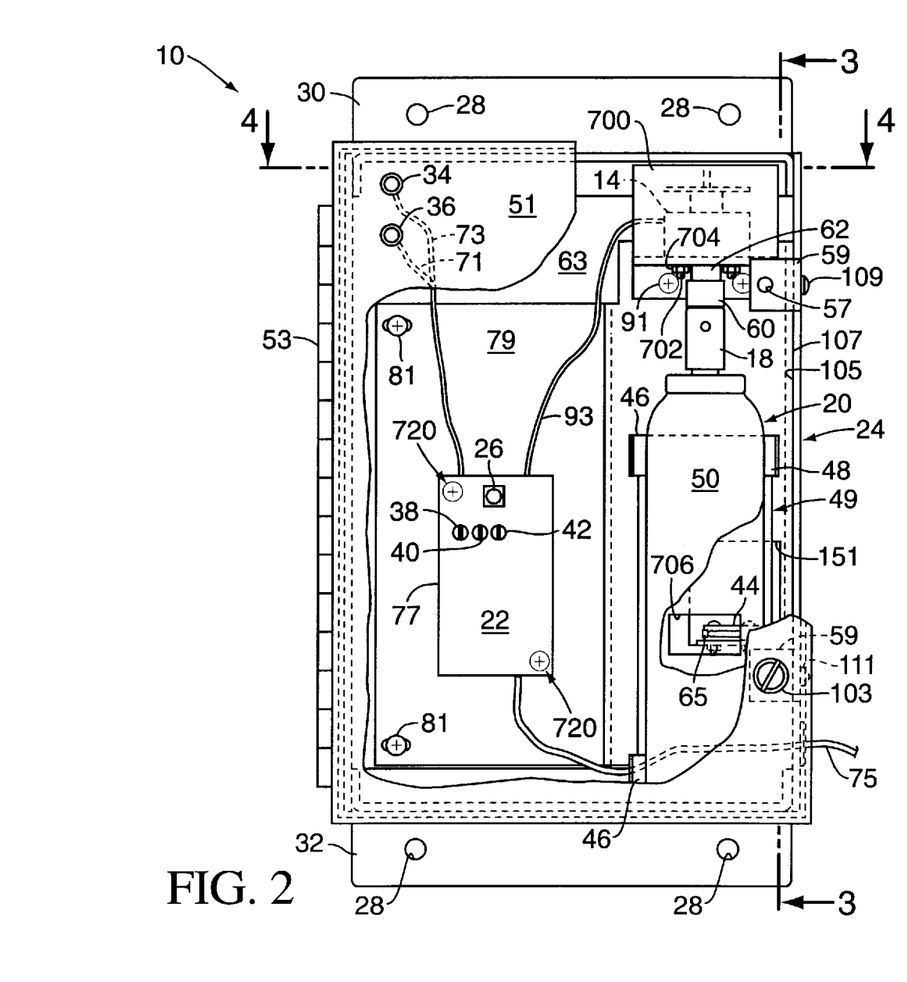
FIG. 2 is a front view of a system provided by the present invention.
Figure 3:
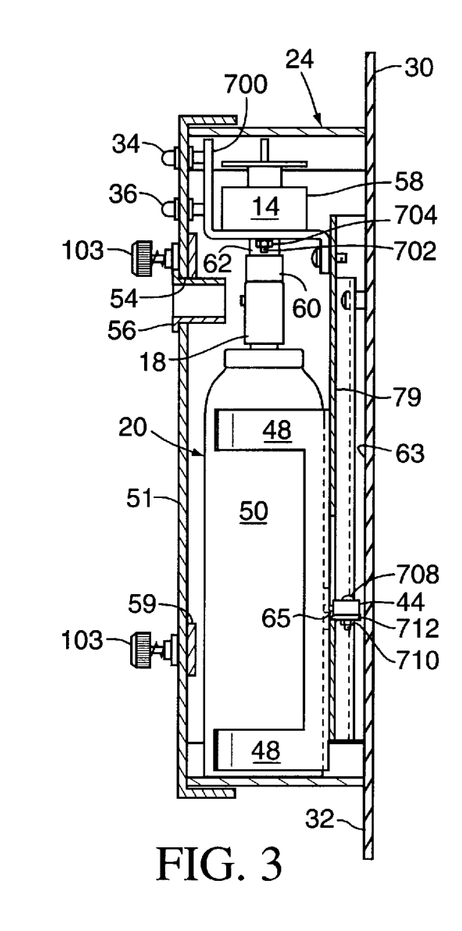
FIG. 3 is a sectional view of the system shown in FIG. 2 taken along the line 3—3.
Figure 4:
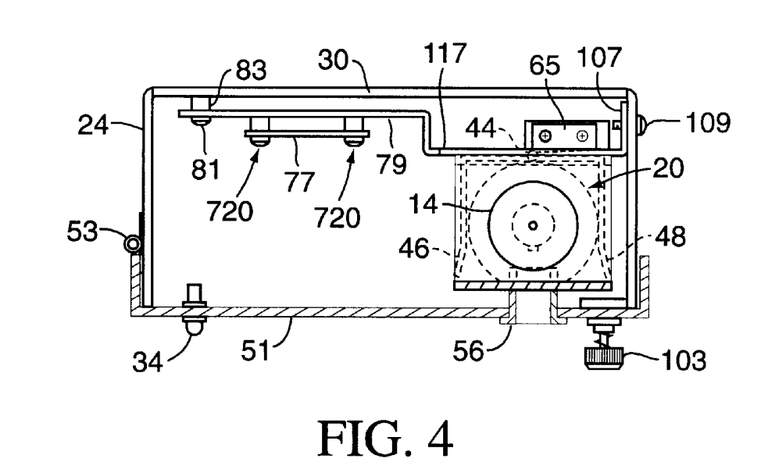
FIG. 4 is a sectional view of the unit shown in FIG. 2 taken along the line 4—4.

FIGS. 2, 3 and 4 show the mechanical components of system 10. A housing 24 contains and protects the mechanical and electrical components, and is mounted to the interior of ductwork 12 using suitable fasteners (not shown) and mounting holes 28 formed in mounting flanges 30 and 32. Mounting flanges 30 and 32 are configured to abut the interior surface of ductwork 12. Housing 24 includes a front door 51 that is attached to housing 24 with a hinge 53, which permits door 51 to be swung open to gain access to the interior of housing 24. Door 51 is secured in its closed position using a pair of slotted spring mounted thumbscrews 103 that are mounted to door 51 and can be threaded through corresponding mounting holes 57 (only one shown) formed in mounting brackets 59, which are mounted to the edge of housing 24.

In vehicles where system 10 can be mounted to the interior of the ductwork 12 m such a way that housing 24 is visible to the driver, a pair of light emitting diodes (LEDs) 34 and 36 is mounted to housing 24. In vehicles where housing 24 is not visible to the user, LEDs 34 and 36 can be mounted to a separately mounted panel (not shown) that can be viewed readily by the driver. LED 36 is illuminated when the ON time count reaches the warning level. LED 34 is illuminated when the ON time count reaches the maximum ON time count, indicating that the container or canister 20 is empty and must be replaced before system 10 will resume operation. A pair of leads 71 and 73 provides electrical communication between LEDs 36 and 34, respectively, and controller 22. Three screw adjustments 38, 40 and 42 are mounted to PC board 77 for controller 22, each of which defines a slot that can be engaged by a screwdriver to rotate the adjustment. Adjustment 38 is rotated to adjust the duration of the ON time cycle. Adjustment 40 is rotated to adjust the duration of the OFF time cycle. Adjustment 42 is rotated to adjust the maximum ON time or spray cycles that are permitted for a container 20 before it must be replaced. Calibration markings can be provided on board 77 around each adjustment 38, 40 and 42. Lead 75 supplies 24 volt DC power from the bus to controller 22.

Controller 22 is formed on PC board 77, which is mounted to mounting plate 79 using screw post assemblies 720. Mounting plate 79 is mounted to the left side of rear wall 63 of housing 24 using screws 81 and mounting posts 83. Plate 79 forms a mounting flange 107, which abuts the right wall 105 of housing 24. A pair of screws 109 and 111 is used to secure mounting flange 107 and plate 79 to right wall 105 of housing 24.

Plate 79 defines a raised canister mounting bed 117, to which a canister mounting 49 is secured in any suitable fashion, such as welding. Canister mounting 49 defines a pair of clips 46 and a pair of clips 48, between which canister or container 20 is removably friction mounted within housing 24. Canister 20 is a commercially available conventional aerosol spray canister, bottle or container that is filled with a vanilla bean deodorizer, the filled canister being available from Pestco, Inc., of Pittsburgh, Pa. Container 20 includes a body 50, which holds the substance to be dispensed, and a spray nozzle 18 that can be actuated to spray the substance through opening 54 formed in housing 24 by exerting a downward force on nozzle 18. A sleeve 56 is friction fit into opening 54. Container 20 can be replaced by unthreading and loosening thumbscrews 103, opening door 51, removing the old container 20 from between clips 46 and 48, and positioning a new container 20 in seat 49 between clips 46 and 48.

Figure 12:
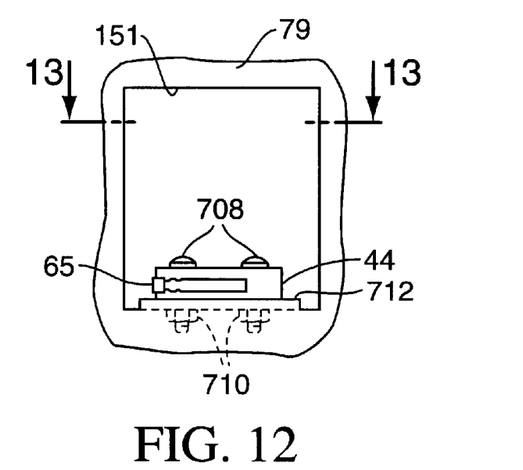
FIG. 12 is a detail side view showing the switch 44 depicted in FIGS. 2, 3 and 4.
Figure 13:
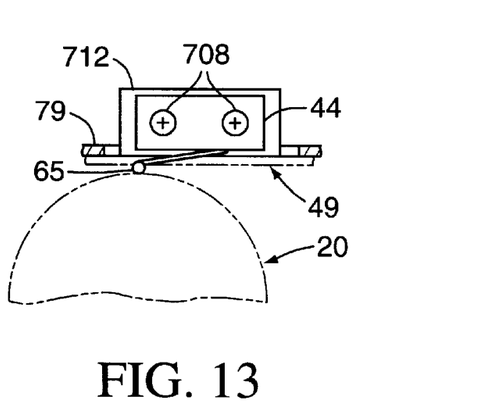
FIG. 13 is a detail top view showing the switch 44 depicted in FIGS. 2, 3 and 4.

A "canister empty" switch 44 is mounted to plate 79. Mounting plate 79 defines an opening 151. Plate 79 defines at the lower boundary of opening 151 a mounting ledge 712, which is formed by bending a section of plate 79. Switch 44 is mounted to ledge 712 using a pair of screws or bolts 708 and nuts 710. Switch 44 is a conventional switch that includes a spring mounted actuation arm 65 that extends through opening 706 formed in plate canister mounting 106. As can be seen best in FIGS. 12 and 13, when canister 20 is mounted in place in mounting 49, arm 65 is depressed by container 20, and switch 44 is closed, indicating that container 20 is mounted in place. When a container 20 is not in place in mounting 49, arm 65 is in its extended position, which indicates that a container 20 is not in place in mounting 49. The state of switch 44 signals to controller 22 the presence or absence of a container 20. Button 65 of switch 44 is depressed, and switch 44 is closed, when a container 20 is mounted in place in mounting 49 between clips 46 and 48. When container 20 is removed from between clips 46 and 48, button 65 is released and extended to its open position, which opens switch 44, which indicates to controller 22 that dispensing cycle cannot continue.

Actuator 14 is a conventional electric actuator or solenoid available from Lucas of Vandalia, Ohio, under the trademark "LEDEX." Actuator includes a pair of threaded mounting posts 702 that are used with nuts 704 to mount actuator 14 to a mounting bracket 700. Mounting bracket 700 is mounted to mounting plate 79 with screws 91. A pair of leads 93 provides electrical communication between actuator 14 and controller 22. Actuator 14 includes a plunger 60 connected to a plunger arm 62. Plunger 60 abuts nozzle 18. Downward movement of plunger 60 depresses nozzle 18 and causes nozzle 18 to spray the substance through opening 54. Actuator 14 includes a body 58 that contains an electric coil that, when energized by a 24 volt DC supply, moves plunger shaft 62 downwardly. Accordingly, energization of the coil of actuator 14 causes downward movement of plunger 60 and actuation of nozzle 18.

Figure 5:
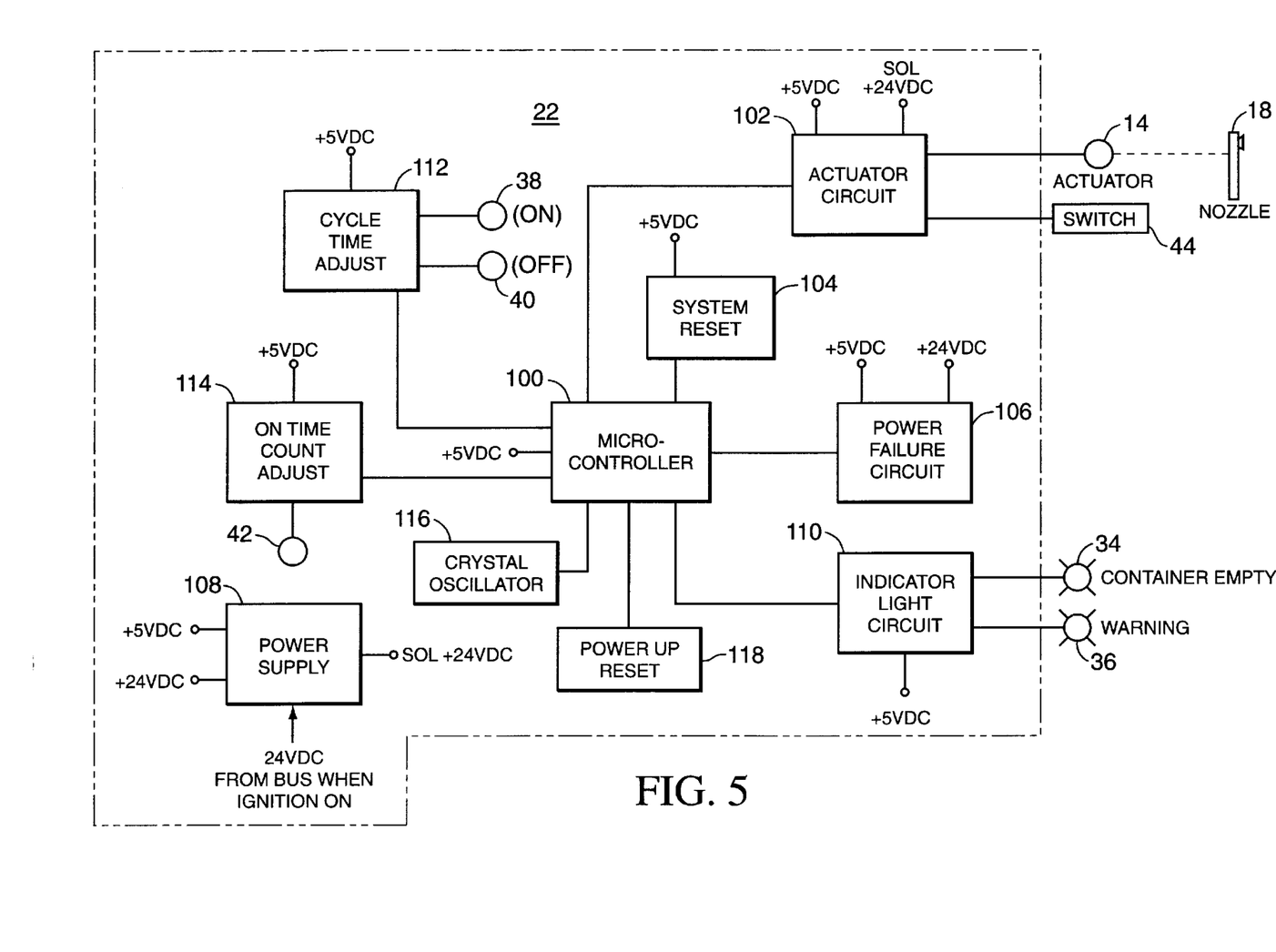
FIG. 5 is a block diagram of the controller and certain other components of the system shown in FIG. 2.

FIG. 5 shows controller 22 in block diagram form, and indicator lights, nozzle actuator 14 and nozzle 18 in schematic form. Controller 22 includes a power supply circuit 108 that receives 24 volt DC power from the bus when the bus ignition is on, and produces regulated 5 volt DC and 24 volt DC at its outputs. Power supply 108 also produces a separate 24 volt DC signal to actuator circuit 102. Controller 22 includes a microcontroller chip 100, which controls the actuation of spray nozzle 18. Preferably, microcontroller 100 is a PIC16F877/PLCC microcontroller IC manufactured by Microchip Technology, Inc., of Chandler, Ariz. As is well known in the art, microcontroller 100 is a programmable controller that includes a number of onboard circuits that can be interfaced, configured and operated to perform various functions through the use of software programmed into microcontroller 100. This software is programmed by the user using assembly language, and is a routine task for someone of ordinary skill in the art. Accordingly, the details of the software on board microcontroller 100 will not be described further. When system 100 is in its spray mode, microcontroller 100 regulates the spray cycles, each of which consists of an ON time or cycle, during which container 20 is spraying the substance, and an OFF time or cycle, during which container 20 is not spraying the substance. System 100 is in its spray mode whenever the bus ignition is on and container 20 is in place in its seat 49, unless the maximum ON time count has been reached, and container 20 has not been removed and a container 20 placed in seat 49. When the maximum ON time count has been reached, container 20 must be removed from seat 49, and a container 20 replaced in seat 49 before system 10 reenters the spray mode (removing container 20 and placing the same, "empty," container 20 back into seat 49 will fool system 10 into assuming a new, full, container 20 has been placed in seat 49, in which case system 10 will reenter the spray mode, even though the "empty" container 20 is still in seat 49). Microcontroller 100 includes timers that monitor the ON time or cycles and the OFF times or cycles to determine when spraying should be commenced and terminated. Spraying is commenced at the end of each OFF time or cycle (and, accordingly, at the commencement of each ON time cycle), and is terminated at the end of each ON time or cycle (and, accordingly, at the beginning of each OFF time or cycle).

Controller 22 includes an actuator circuit 102 through which microcontroller 100 controls the operation of actuator 14. A system reset 104 is provided to permit the user to reset the ON time count in appropriate circumstances. For example, the ON time count should be reset when a damaged container 20 must be removed and replaced before its maximum ON time count has been reached. Upon loss of 24 volt DC power from the bus (due to either a malfunction in the bus or the switching off of the bus ignition) power supply 108 maintains the 5 volt DC output long enough to permit a power failure circuit 106 to detect the loss of power and cause microcontroller 100 to store in EEPROM in microcontroller 100 the ON time count and the ON time or cycle and OFF time or cycle durations. An indicator light circuit 110 is used by microcontroller 100 to energize indicators 34 and 36. Cycle time adjust circuit 112 is used to adjust the duration of the ON time or cycle using screw adjustment 38, and the duration of the OFF time or cycle using screw adjustment 40. ON time count adjust 114 is used to adjust the maximum ON time count level at which microcontroller 100 will assume that container 20 is empty. This level is adjusted using screw adjustment 42. A crystal oscillator 116 maintains timing for microcontroller 100 at 5.06 megahertz. A power up reset circuit 118 prevents microcontroller from becoming operational until all components of microcontroller 100 have 5 volt DC supply available and are ready to function.

Figure 6:
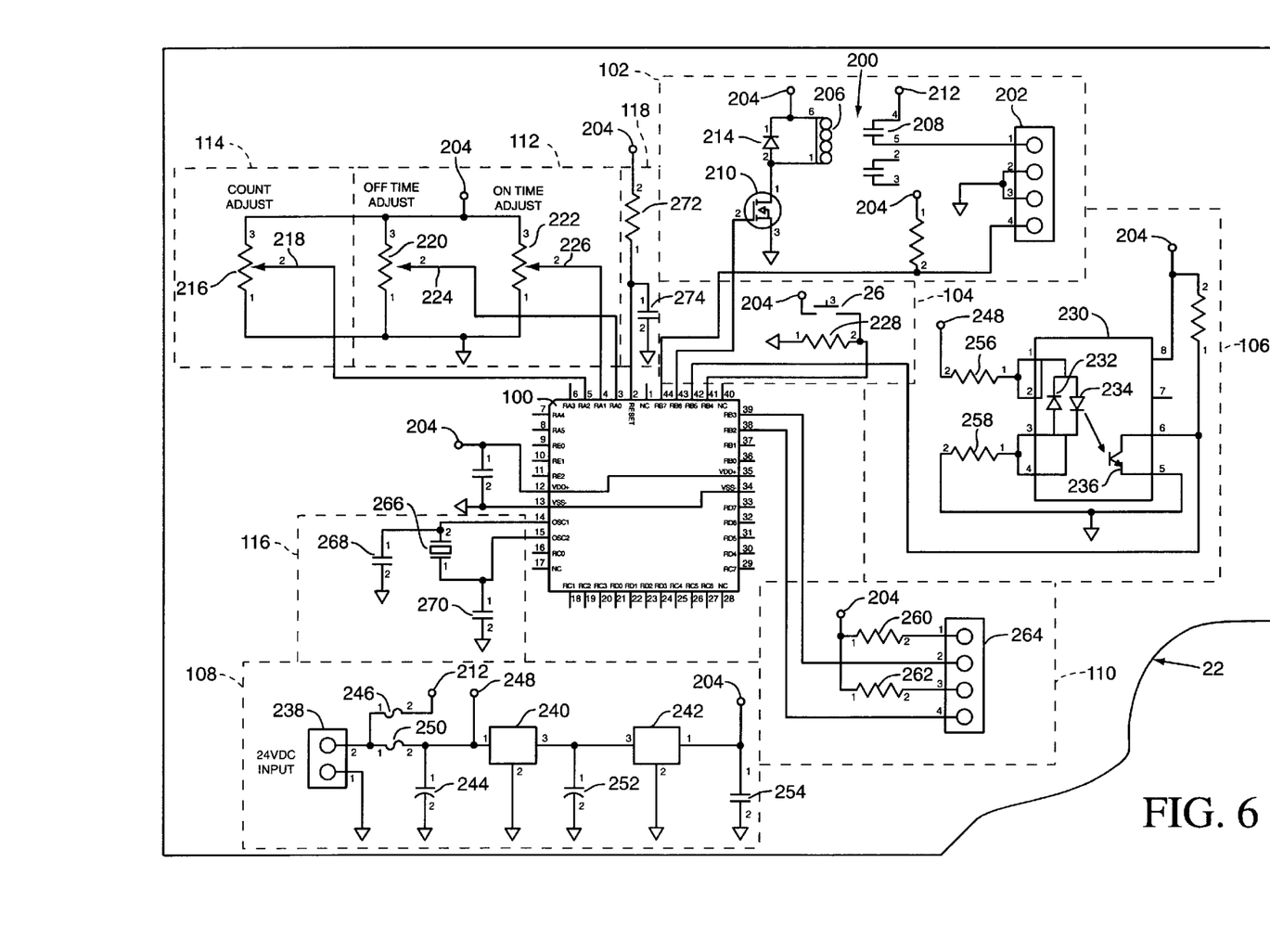
FIG. 6 is a schematic view of the details of the controller shown in FIG. 5.

FIG. 6 shows controller 22 in schematic form. Actuator 14 is connected across pins 1 and 2 of 4 pin connector or strip 202 of actuator circuit 102. Microcontroller 100, through the software programmed into it, applies the SOL 24 volt DC signal at 212 to actuator 14 through actuator circuit 102 by applying a signal to pin 43 (RB6) of microcontroller 100 that operates field effect transistor, or FET, 210 (which can be a VN10KM as a switch. During the ON time or cycle microcontroller produces a signal on pin 43 that closes FET 210, and the 5 volt DC signal at 204 is applied to the coil 206 of relay 200. Application of the 5 volt DC signal at 204 to coil 206 of DSP1E relay 200 (manufactured by Aromat Corporation of New Providence, N.J.) causes normally open contacts 208 of relay 200 to close, thereby applying the SOL 24 volt DC signal from 212 of power supply 108 to pin 1 of connector 202 through relay 200 of actuator circuit 202. Application of the SOL 24 volt DC signal to pin 1 of connector or strip 202, to which actuator 14 is connected, causes actuator 14 to depress nozzle 18 and spray the substance from container 20. Microcontroller 100 uses an internal timer to track the ON time or cycle, and produces a signal at pin 43 that opens FET 210 when the ON time cycle expires, which removes the 5 volt DC signal from coil 206, thereby opening contacts 208 and removing the SOL 24 volt DC signal from pin 1 of strip 202. Microcontroller 100 uses an internal timer to track the OFF time or cycle, and closes FET 210 at the end of the OFF time cycle to begin another ON time or cycle. At the end of the ON time or cycle, actuator 14 is deenergized, nozzle 18 is released, and spraying from container 20 ceases until the beginning of the next ON time or cycle. Diode 214 ensures that the "kickback" caused by the collapsing electromagnetic field when coil 206 is deenergized does not damage FET 210 or microcontroller 100.

Pin 4 of connector 202 of actuator circuit 102 is connected to pin 44 (RB7) of microcontroller 100. Pin 3 and 4 of connector 202 are also connected to switch 44. Microcontroller 100 periodically polls switch pin 44 to determine the status (open or closed) of switch 44. When switch 44 is closed (as it will be when the container 20 is mounted in place in holder 49), pins 3 and 4 are shorted together through switch 44, and the voltage on pin 44 of microcontroller 44 is at ground, which enables microcontroller 100 to continue or initiate the spray cycle. When the container 20 is removed from holder 49, switch 44 opens, and pin 44 goes to 5 volts DC, which commands the software in microcontroller 100 to suspend the series of ON time signal transmitted to FET 210 until container 20 is replaced.

ON time count adjust 114 includes a potentiometer 216, which is used to adjust the maximum ON time count. Wiper 218 of potentiometer 216 is physically attached to screw adjustment 42 which, when it is rotated, moves wiper 218 across potentiometer 216 to adjust the voltage at pin 5 (RA2) of microcontroller 100 to which it is electrically connected to a level between 0 and 5 volts DC. The software in microcontroller 100 configures the components at pin 5 to operate as an eight bit analog to digital, or A/D, converter. The A/D converter converts the analog signal appearing at pin 5 to a digital signal, the value of which is related to the level of the analog signal on pin 5. Accordingly, rotating adjustment 42 increases or decreases the analog voltage on pin 5 (depending on which direction adjustment 42 is rotated), thus increasing or decreasing the digital signal produced by the A/D converter. The range of possible maximum ON time count levels available is set in memory in microcontroller 100 at the factory. This range is typically 1,500 to 2,500 ON time cycles. Microcontroller 100 then converts the digital signal to the maximum ON time count level by calculating the ratio of the value of the digital signal to 256, multiplying that ratio by 1,000, and adding the result to 1,500. If, for example, the user wishes to set the maximum ON time count level to 2,000 cycles, the user will turn the adjustment to 2,000, which will set wiper 218 to the midpoint of potentiometer 216. This will cause a 2.5 volt DC signal to be applied to pin 5 of microcontroller 100. The A/D converter will convert the 2.5 volt DC signal at pin 5 to a digital signal having a value of 128, which microcontroller 100 will interpret as a command to set the maximum ON time count level to 2,000. A 0.9960935 volt DC signal at pin 5 would be converted to a digital value of 51, and a command to set the maximum ON time count level to 1,700.

Cycle time adjust circuit 112 uses the same approach to adjust the ON time cycle and the OFF time cycle. The range of values for the OFF time cycle will typically be set in microcontroller 100 at the factory to 1 to 30 minutes, while the ON time cycle typically will be set to 1 to 5 seconds. Rotation of screw adjustment 38 adjusts the ON time cycle by moving wiper 226 of potentiometer 222 to adjust the voltage appearing at pin 4 (RA1) of microcontroller 100, and rotation of screw adjustment 40 adjusts the OFF time cycle by moving wiper 224 of potentiometer 220 to adjust the voltage appearing at pin 3 (RA0) of microcontroller 100. Microcontroller 100 has timers that the software starts at the beginning of the ON times and the OFF times, which are used by the software in microcontroller 100 to determine when the ON times and the OFF times have expired.

System reset 104 includes a system reset switch 26, which is used to reset the ON time count to zero. Switch 26 is located on the PC board containing controller 22, and is available to the user. Operation of switch 26 causes a 5 volt DC signal to be applied to pin 41 (RB4) of microcontroller 100, which the software of microcontroller 100 interprets as a command to reset the ON time count to zero, which it then does. 100 kohm resistor 228 bleeds static and other spurious noise from pin 41 to prevent inadvertent resets of the ON time count.

Power supply 108 receives 24 volt DC power from the bus at pin 2 of connector 238. A 470 microfarad capacitor 244 stabilizes the 24 volt DC signal appearing at pin 2 of connector 238. An AGX4 fuse 246 protects the circuit connected the SOL 24 volt DC supply at 212. An AGX1 fuse 250 protects the circuits connected to 5 volt DC supply 204 and 24 volt DC supply 248. A 12 volt DC LM7812 voltage regulator 240 receives the 24 volt DC signal from pin 2 of connector 238 at pin 1 and produces regulated 12 volt DC power at pin 3. A 470 microfarad capacitor 252 stabilizes the 12 volt DC signal. This signal is applied to pin 3 of a 5 volt DC LM7805 voltage regulator 242, which produces a regulated 5 volt DC signal at pin 1 and 204. A 0.22 microfarad capacitor 254 stabilizes this 5 volt DC signal.

Power failure circuit 106 includes an MID400 opticoupler chip 230. Opticoupler 230 includes a pair of light emitting diodes, or LED's, 232 and 234, and a light activated transistor 236 which is operated as a switch. When 24 volt DC power is available at 248, current is flowing through LED's 232 and 234, LED's 232 and 234 produce light, and this light biases transistor 236 on to maintain transistor 236 closed. When transistor 236 is closed, pin 6 of opticoupler 230 and pin 42 (RB5) of microcontroller 100 are at ground potential, which the software of microcontroller 100 interprets as the availability of 24 volt DC power. When a power loss occurs, 24 volt power at 212 and 248 will begin to drop. When the power level at 248 drops sufficiently, the current flowing through LED's 232 and 234 will be insufficient to produce enough light to maintain transistor 236 closed. When that occurs, 204 will still be at 5 volts DC due to the charges on capacitors 244, 252 and 254. Transistor 236 will open, and pin 6 of opticoupler 230 and pin 42 of microcontroller 100 will go to the 5 volts DC level still available temporarily at 204. The software in microcontroller 100 interprets the presence of a 5 volt DC signal at pin 42 as a loss of power, and the software will store the current values of the ON time count and the ON and OFF cycle times. When power is made available (due to either repairing the bus malfunction or turning on the bus ignition), microcontroller 100 will check memory to determine whether values for the ON time count and the ON and OFF cycle times. The software in microcontroller 100 interprets the absence of these values as a first time startup of system 10. It interprets the presence of these values as a resumption of operation, and it uses the values stored in the operation of system 10. 1 kohm resistors 256 and 258 limit the current through LED's 232 and 234. Indicator light circuit 110 is used to control illumination of ON time warning level LED 36 and container empty (maximum ON time level) LED 34. When the warning count level is reached, the software in microcontroller 100 closes a switch in microcontroller 100, which allows the 5 volt DC supply at 204 to be applied to warning LED 36 connected to pins 1 and 2 of connector 264 through pin 39 (RB3) of microcontroller 100. When the maximum count level is reached, the software in microcontroller 100 closes another switch in microcontroller 100, which allows the 5 volt DC supply at 204 to be applied to warning LED 36 connected to pins 3 and 4 of connector 264 through pin 38 (RB2) of microcontroller 100. The ON time count is also reset to zero. Indicator light circuit 110 also includes a pair of current limiting 475 ohm resistors 260 and 262, which are connected between the 5 volt DC signal at 204 and pin 1, and pin 3, respectively, of connector 264.

Crystal oscillator circuit 116 includes a CR505M crystal 266, which provides the 5.06 MHz timing for microcontroller 100 through pins 14 and 15 (OSC1 and OSC2). The clock circuit that actually operates crystal 266 is on board microcontroller 100. 47 picofarad capacitors 268 and 270 provide stability for crystal 266, maintaining it at 5.06 MHz.

When microcontroller 100 is powered up, power up circuit 118 causes it to come up in "reset" for a short period of time. During the "reset" period, the software in microcontroller 100 prevents microcontroller 100 from functioning until all components of microcomputer 100 are powered and rendered functional. Application of the 5 volt DC signal from 204 to pin 2 (RESET) causes the software to allow microcontroller 100 to begin functioning. The reset period is imposed by a 100 kohm resistor 272 and a 22 microfarad capacitor 274, which form a time delay circuit. The time delay circuit causes pin 2 of microcontroller 100 to delay reaching 5 volts DC until after pin 12 (VDD+; main 5 volt DC supply) of microcontroller 100 reaches 5 volts DC. Once pin 2 receives the 5 volt DC signal, the software in microcontroller 100 allows microcontroller 100 to begin functioning.

Microcontroller 100 monitors the ON time count. When the ON time count reaches the warning level, warning light 36 is energized. When the maximum ON time count is reached, microcontroller 100 energizes the container empty light 34, and disables the system until switch 44 is opened, which microcontroller 100 interprets as removal of the empty container 20, and switch 44 is subsequently closed, which microcontroller 100 interprets as insertion of a new, full container 20 in mounting 49. If switch 44 is opened before the ON time count reaches the maximum ON time count, but the ON time count is greater than a preset replacement threshold (which is between the warning level and the maximum level), the software in microcontroller 100 assumes that the user is replacing a nearly empty container 20 with a full container 20, and microcontroller 100 resets the ON time count to zero. The replacement threshold may be set at 1,800 ON times or cycles, and operation of the spraying cycles commenced when switch 44 is reclosed by insertion of another container 20 in mounting 49. If switch 44 is determined to have been opened and the ON time count is less than the replacement threshold, the spraying cycle is resumed upon reclosure of switch 44 at the ON time count existing at the time switch 44 was opened.

Figure 7:
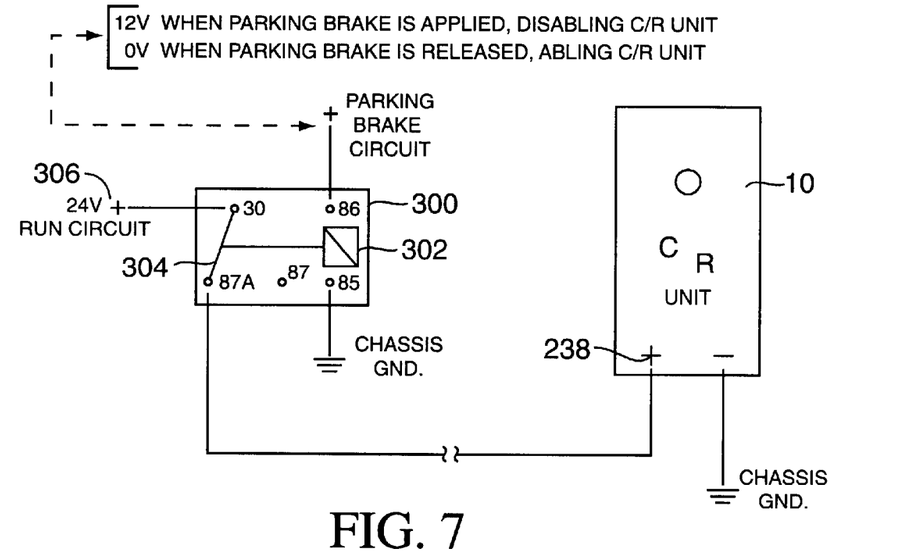
FIG. 7 shows in schematic form the relationship between the system shown in FIGS. 2, 3 and 4 and the electrical system of a NOVA bus when the system is configured to be operational only when the bus ignition is on and the parking brake is off.

FIG. 7 shows the relationship between system 10 and the electrical system of a NOVA bus (manufactured by Nova of Canada) when system 10 is configured to operate only when the ignition is on and the parking brake is off. In this configuration, a single throw mini relay 300 is connected to system 10, and system 10 receives its 24 volt DC supply from relay 300, rather than directly from the bus ignition. Depending on the type of bus in which system 10 is installed, 300 may be already present as a component of the electrical system of the bus, or it may not be present, in which case it will have to be added to the bus. The rating of relay 300 should match the voltage available from the parking brake circuit bus (for example, the parking brake circuit of an ORION bus—manufactured by Orion Industries of Los Angeles, Calif.—provides a 24 volt DC signal). Relay 300 must be added to the bus circuit for an ORION or NOVA bus. In FIG. 7, 12 volts DC is available from the parking brake circuit of the NOVA bus, so a 12 volt relay 300 is used. Relay 300 receives the 24 volt DC supply 306 for system 10 at pin 30. Relay 300 includes a coil 302 connected across pins 85 (+24 volt DC) and 86 (ground) of relay 300, which operates contact 304. Contact 304 is connected to pin 30 of relay 300, and is in its open state when it is positioned on pin 87, and in its closed state when it is positioned against pin 87A of relay 300. Pin 86 of relay 300 is connected to the parking brake circuit, and in particular, to a connection of the parking brake circuit that is either at 12 volts DC, when the parking brake is applied, or at 0 volts DC, when the parking brake is off. When the parking brake is applied, a 12 volt DC signal is applied to pin 86 of relay 300, which energizes coil 302 and moves contact 304 to its open state. In its open state, contact 304 is positioned against pin 87 of relay 300, and the 24 volt DC supply 306 is disconnected from system 10, disabling it to prevent it from dispensing the substance. When the parking brake is released, the voltage on pin 86 drops to 0 volts DC, coil 302 is deenergized, and contact 304 moves back to its closed state. In its closed state, contact 304 is positioned against pin 87A of relay 300, and the 24 volt DC supply 306 is applied to connector 238 of power supply 108 of system 10 to enable system 10 to produce ON time cycles to dispense the substance from container 20. In this configuration, power to system 100 will be lost when there is a malfunction that causes a loss of 24 volt DC power from the bus, when the bus ignition is turned off, or when the parking brake is applied, in which cases power failure circuit 106 will store the ON time count and the ON and OFF time durations in microcontroller 100 to facilitate resumption of spraying when 24 volt DC power returns.

Figure 8:
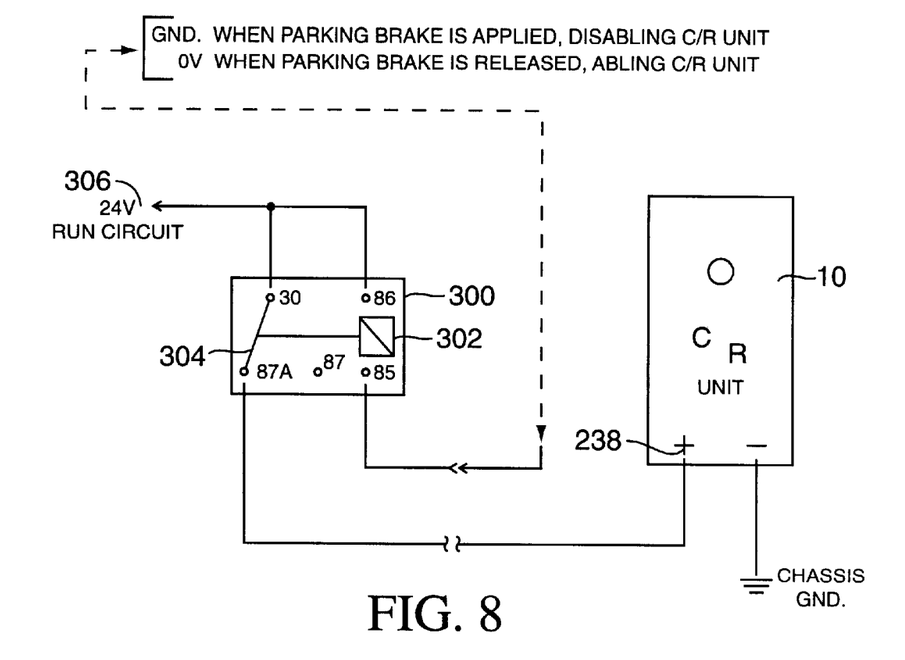
FIG. 8 shows in schematic form the relationship between the system shown in FIGS. 2, 3 and 4 and the electrical system of a FLEXIBLE bus when the system is configured to be operational only when the bus ignition is on and the parking brake is off.

FIG. 8 shows the relationship between system 10 and the electrical system of a FLEXIBLE bus model no. 40102-4T (50) and model no. 40102-D50 (manufactured by Flexible Corporation of Delaware, Ohio) when system 10 is configured to operate only when the ignition is on and the parking brake is off. The configuration is similar to that shown in FIG. 7, with the exceptions that relay 300 is a 24 volt relay, and is operated by a parking brake circuit that provides a 0 volt DC signal to pin 85 when the parking brake is off to energize coil 302 and enable system 10, and connects pin 85 to ground when the parking brake is on to deenergize coil 302 and disable system 10.

Figure 9:
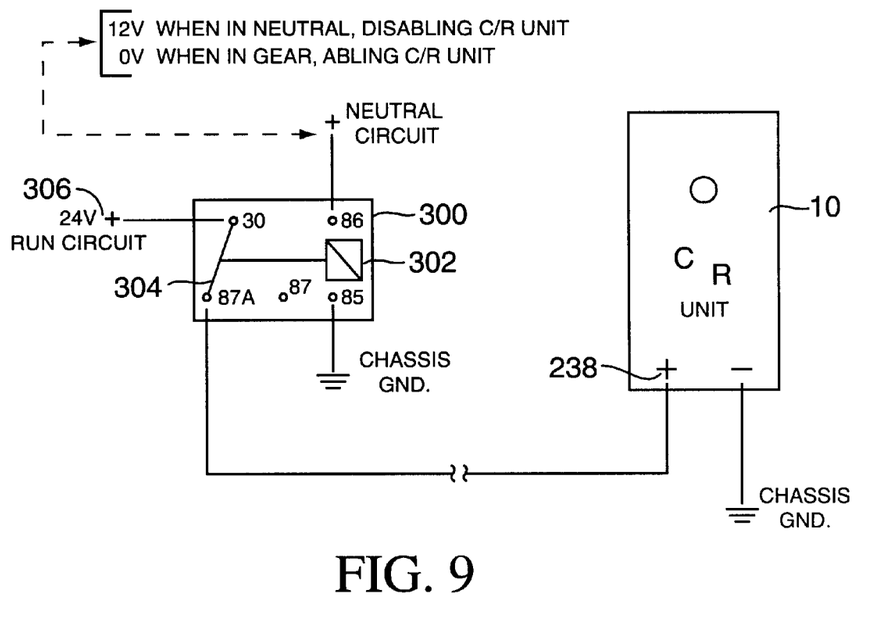
FIG. 9 shows in schematic form the relationship between the system shown in FIGS. 2, 3 and 4 and the electrical system of a NOVA bus when the system is configured to be operational only when the bus ignition is on and the bus is in gear.

FIG. 9 shows the relationship between system 10 and the electrical system of a NOVA bus when system 10 is configured to operate only when the ignition is on and the bus is in gear. Relay 300 must be added to the bus circuit. Operation and configuration of the circuit shown in FIG. 9 is identical to that shown in FIG. 7, with the exceptions that the signal applied to pin 86 is derived from the neutral circuit of the bus, rather than the parking brake circuit. System 10 is enabled when the bus is in gear, which causes a 0 volt DC signal to be applied to coil 302, causing contact 304 to open.

Figure 10:
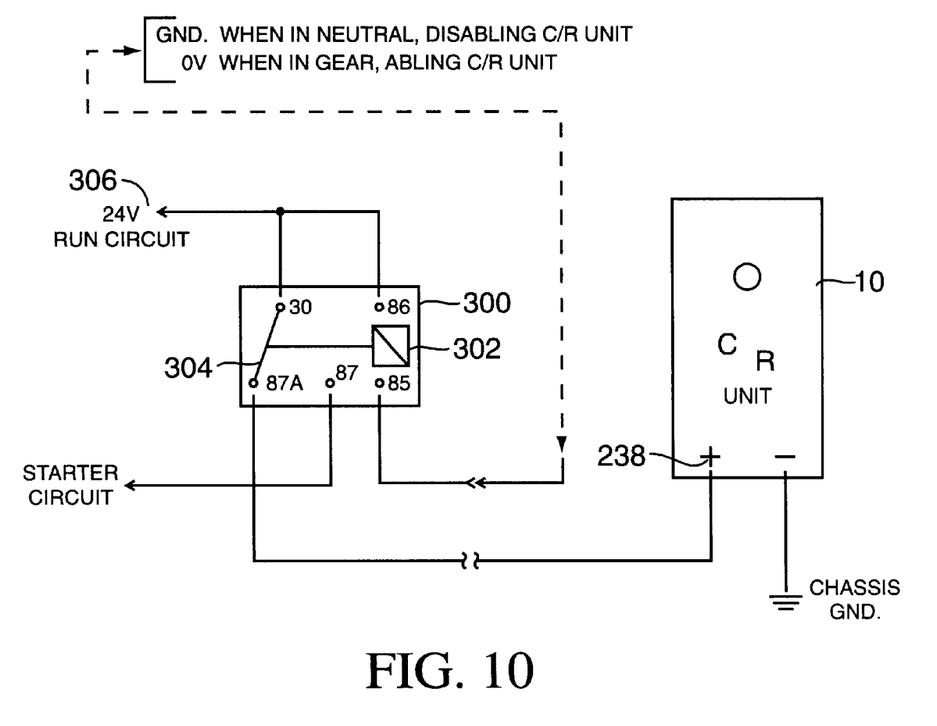
FIG. 10 shows in schematic form the relationship between the system shown in FIGS. 2, 3 and 4 and the electrical system of an ORION bus when the system is configured to be operational only when the bus ignition is on and the bus is in gear.

FIG. 10 shows the relationship between system 10 and the electrical system of an ORION bus when system 10 is configured to operate only when the ignition is on and the bus is in gear. The configuration shown in FIG. 10 is identical in construction and operation to that shown in FIG. 8, with the exceptions that the relay 300 already is part of the electrical circuit of the bus, there is a pre-existing connection between pin 87 and the starter circuit, and pin 85 is connected to the neutral circuit rather than the parking brake circuit. When this configuration is used with a FLEXIBLE bus of the type described above, relay 300 must be added, and there is no pre-existing connection between pin 87 and the starter circuit.

Figure 11A:
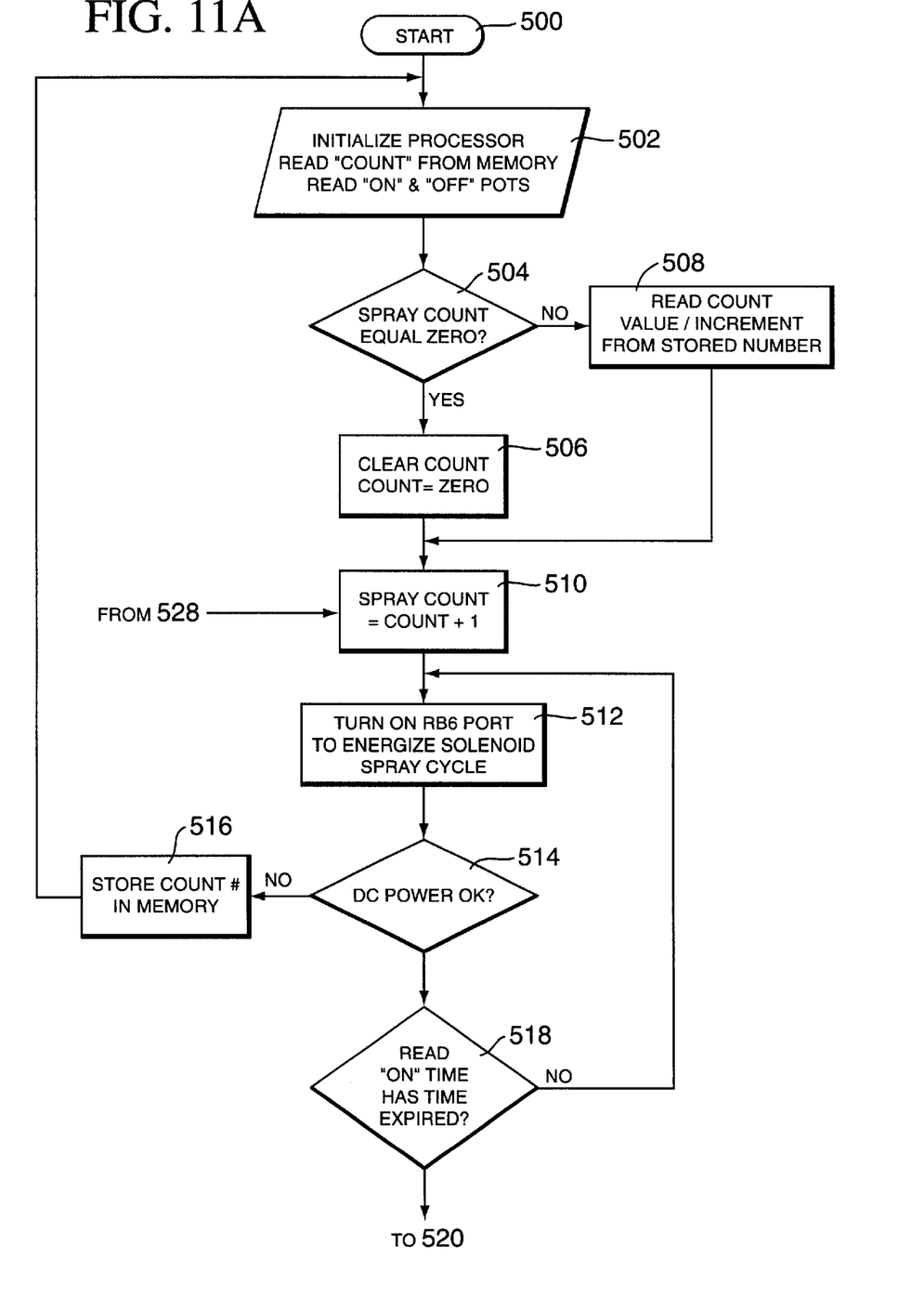
FIG. 11 shows in block diagram form the software that is contained in the microcontroller for the controller shown in FIG. 5.
Figure 11B:
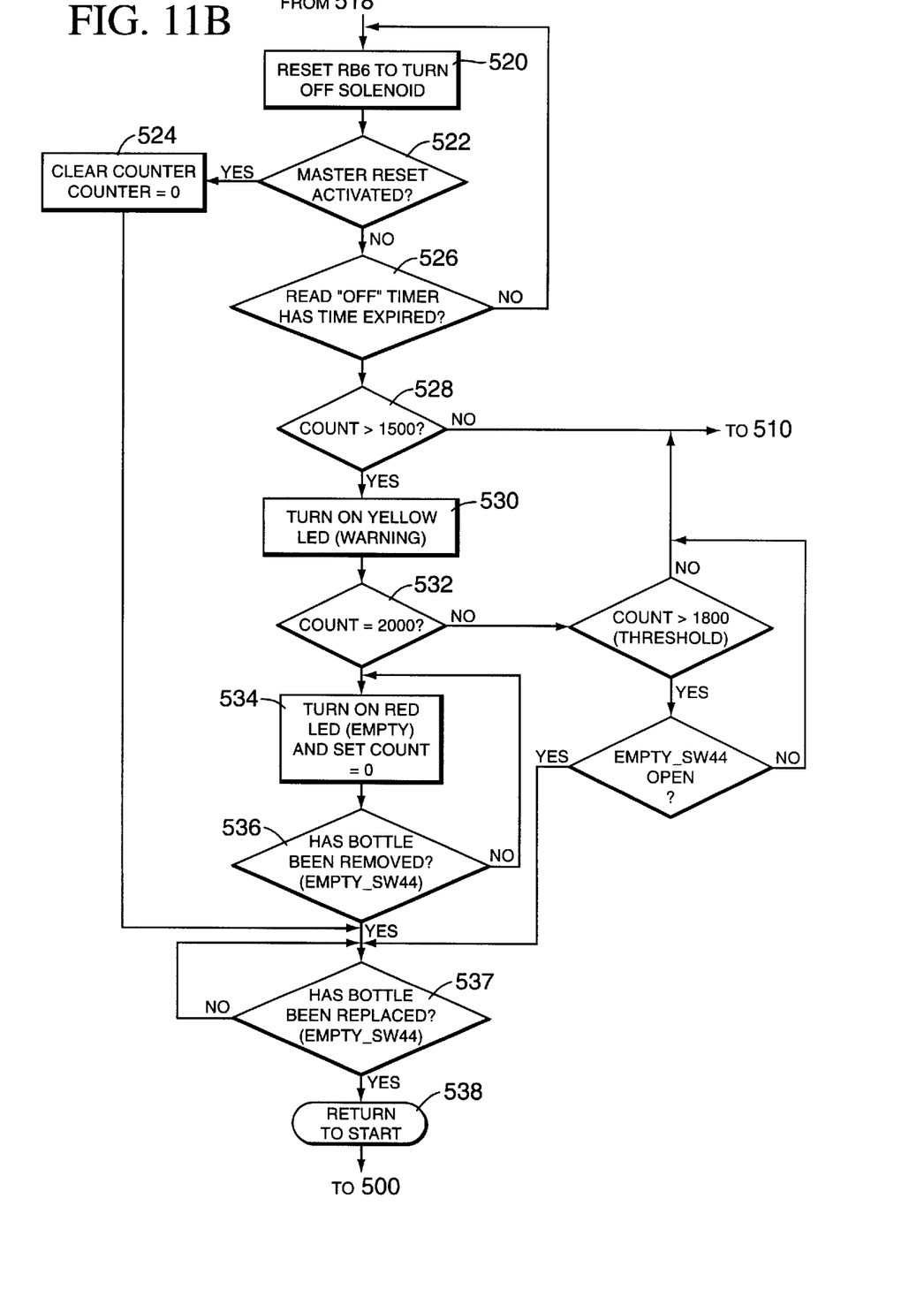

FIG. 11 shows the software contained in microcontroller 100. The software is started at block 500. At block 502 microcontroller 100 reads from memory the current ON time count and the ON and OFF time durations. At block 504, microcontroller 100 determines whether the ON time count is zero, indicating a first time startup of controller 22. If the ON time count is zero, the ON time count is cleared at block 506. If the ON time count is not zero, the ON time count is read and stored at block 508. At block 510, the ON time count is incremented by 1 to reflect the upcoming occurrence of an ON spray cycle. At block 512, pin 43 of microcontroller 100 is turned on to initiate a spray cycle. At block 14, the software determines whether 24 volt DC power is available. If not, the ON time count is stored at block 516, and processing passes to block 502. If 24 volt DC power is available, the ON time is read and block 518 compares this reading to the ON time duration to determine whether the ON time has expired. If it has, the ON cycle must be terminated, and block 520 turns off pin 43. If the ON time duration has not expired, processing passes to block 512, until the ON time expires.

At block 522, microcontroller 100 determines whether master reset 26 has been activated. If it has, indicating that the ON time count must be reset to zero, block 524 sets the ON time count to zero and processing passes to block 500. If the master reset 26 has not been activated, block 526 reads the OFF time timer and determines whether the OFF time cycle has expired. If it has not expired, processing passes to block 520 until the OFF time cycle expires. If the OFF time cycle has expired, block 528 reads the ON time count and determines whether the ON time count has reached the warning level (in this case, 1,500 sprays). If it has not been reached, processing passes to block 510, where the ON time count in incremented by one, and a new ON time spray cycle is initiated. If the warning level has been reached, yellow warning LED 36 is energized by block 530, and block 532 determines whether the container empty level (in this case, 2,000 sprays) has been reached. If the container empty level has been reached, the yellow warning light 36 is extinguished, the red container empty LED 38 is energized by block 534, and the ON time count is set to zero. Block 536 determines whether the empty container 20 has been removed by checking the status of switch 44. If switch 44 has been opened, block 537 determines whether container 20 has been replaced. If container 20 has been replaced, the container empty light 34 is extinguished and processing passes to block 500 to begin spraying with a new container 20 and an ON time count equal to zero. If container 20 has not been removed, processing passes to block 534 until switch 44 is opened. If the maximum ON time count has not been reached, processing passes to block 533, which determines whether the ON time count has reached the empty threshold of 1,800 cycles. If it has not, processing passes to block 510 to initiate another ON spray cycle. If the ON time count has reached the empty threshold, block 535 determines whether the container 20 has been removed (as indicated by the status of switch 44). If container 20 has been removed, the software assumes the user is replacing container 20 with a full container 20, and processing passes to block 536.

What is claimed is:

1. A dispensing system for dispensing a substance comprising:

a canister including a body that contains a substance to be dispensed from said canister, a nozzle through which the substance is dispensed and an electric actuator mounted to said nozzle;

a controller that controls dispensing of the substance from said canister, said controller controlling operation of said canister during a dispensing cycle that includes an ON time during which said controller actuates said actuator to dispense the substance from said canister, and an OFF time during which said controller deactivates said actuator to stop dispensing of the substance from said canister; and a counter that accumulates the duration of said ON times occurring.

2. The dispensing system recited by claim 1 wherein said system is mounted in a vehicle.

3. The dispensing system recited by claim 2 wherein said system is mounted in the heating and air conditioning ductwork of the vehicle to permit the heating and air conditioning system of the vehicle to convey the substance throughout the interior of the vehicle.

4. The dispensing system recited by claim 2 wherein the vehicle is a bus.

5. The dispensing system recited by claim 2 wherein said system can cause said dispensing cycle to occur only if the ignition system of the vehicle is on.

6. The dispensing system recited by claim 6 wherein said system provides an indication that the count tallied by said counter has reached a predetermined level.

7. The dispensing system recited by claim 1 wherein said system stops dispensing when the count tallied by said counter reaches a predetermined level until said canister is replaced by another canister.

8. The dispensing system recited by claim 1 wherein said counter counts the number of said ON times.

9. A method for dispensing a substance including the steps of:

mounting a dispenser containing the substance in the space in which the substance is to be dispensed;

mounting an actuator in operable relationship with the dispenser, actuation of the actuator causing the dispenser to dispense the substance;

actuating the dispenser cyclically, each cycle including an on time of a preselected duration during which the actuator is actuated to cause dispensing, and an off time of a preselected duration during which the actuator is not actuated; and counting the number of occurrences of on times.

10. The method recited by claim 9 wherein the dispenser is actuated cyclically only upon the occurrence of a condition.

11. The method recited by claim 10 wherein the dispenser is mounted in the ductwork of a vehicle to permit the heating and air conditioning systems of the vehicle to disperse the dispensed substance throughout the interior of the vehicle.

12. The method recited by claim 11 wherein the dispenser is actuated only when the vehicle parking brake is released.

13. The method recited by claim 12 wherein the dispenser is actuated only when the vehicle is in gear.

14. The method recited by claim 13 further comprising the step of providing an indication that said number of occurrences of on times has reached a predetermined level.

15. The method recited by claim 9 further comprising the step of suspending further actuation of said dispenser when said number of occurrences of on times reaches a predetermined level until said dispenser is replaced by another dispenser.

* * * * *